United States Patent
Hull et al.

(10) Patent No.: US 10,830,027 B2
(45) Date of Patent: Nov. 10, 2020

(54) SYSTEM AND METHOD TO EVALUATE KEROGEN-RICH SHALE

(71) Applicant: Saudi Arabian Oil Company, Dhahran (SA)

(72) Inventors: Katherine Leigh Hull, Houston, TX (US); Younane N. Abousleiman, Norman, OK (US); Shannon L. Eichmann, Katy, TX (US); David Jacobi, Spring, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/384,186

(22) Filed: Apr. 15, 2019

(65) Prior Publication Data

US 2020/0325758 A1  Oct. 15, 2020

(51) Int. Cl.
*E21B 43/247* (2006.01)
*E21B 49/02* (2006.01)
*E21C 41/16* (2006.01)
*G01N 3/06* (2006.01)
*E21B 49/00* (2006.01)

(52) U.S. Cl.
CPC .......... *E21B 43/247* (2013.01); *E21B 49/02* (2013.01); *E21C 41/16* (2013.01); *G01N 3/062* (2013.01); *G01N 3/066* (2013.01); *E21B 49/003* (2013.01)

(58) Field of Classification Search
CPC ...... E21B 43/247; E21B 49/02; E21B 49/003; E21C 41/16; G01N 3/062; G01N 3/066
USPC .... 250/306, 307, 309, 310, 311; 850/21, 22, 850/33, 37, 38, 39, 40
See application file for complete search history.

(56) References Cited

U.S. PATENT DOCUMENTS

| | | | |
|---|---|---|---|
| 3,456,183 A * | 7/1969 | Codrington | G01N 24/081 324/303 |
| 6,411,902 B1 | 6/2002 | Wiltshire | |
| 7,983,845 B2 | 7/2011 | Minh | |
| 8,278,931 B2 | 10/2012 | Fang et al. | |
| 8,473,213 B2 | 6/2013 | Zhu et al. | |
| 8,729,903 B2 | 5/2014 | Srnka et al. | |
| 9,057,797 B2 | 6/2015 | Omeragic et al. | |
| 9,152,745 B2 | 10/2015 | Glinsky | |
| 9,784,882 B2 | 10/2017 | Vinegar et al. | |
| 2013/0013209 A1 | 1/2013 | Zhu et al. | |
| 2013/0238304 A1 | 9/2013 | Glinsky | |
| 2013/0341028 A1* | 12/2013 | Christian | C09K 8/032 166/305.1 |
| 2014/0048694 A1 | 2/2014 | Pomerantz | |

(Continued)

FOREIGN PATENT DOCUMENTS

| | | |
|---|---|---|
| EP | 247669 | 12/1987 |
| WO | WO 2018170035 | 9/2018 |

OTHER PUBLICATIONS

Hull and Abousleiman, "New Frontiers in Oil and Gas Exploration," Chapter 10: Insights of the Rev of Source Shale from Nano- and Micromechanics, Springer International Publishing Switzerland, 2016, 29 pages.

(Continued)

*Primary Examiner* — Nicole M Ippolito
(74) *Attorney, Agent, or Firm* — Fish & Richardson P.C.

(57) ABSTRACT

A system and method for evaluating kerogen-rich shale (KRS) including measuring, via scanning microscopy, electrical conductivity of a KRS sample and a mechanical property of the KRS sample.

38 Claims, 6 Drawing Sheets

(56) References Cited

U.S. PATENT DOCUMENTS

2016/0017202 A1* 1/2016 Yang .................. C09K 8/82
166/250.01
2017/0067836 A1* 3/2017 Hull .................. G01N 23/2251
2017/0336528 A1 11/2017 Badri et al.

OTHER PUBLICATIONS

PCT International Search Report and Written Opinion issued in International Application No. PCT/US2020/028070 dated Aug. 25, 2020, 17 pages.

Nottenburg et al., "Temperature and stress dependence of electrical and mechanical properties of Green River oil shale," Fuel, IPC Science and Technology Press, 58:2 (144-148), Feb. 1, 1979, 5 pages.

Shabro et al., "Pore-scaling modeling of electrical resistivity and permeability in FIB-SEM images of organic mudrock," Geophysics, Society of Exploration Geophysicists 79:5 (D289-D299), Sep.-Oct. 2014, 11 pages.

Shukla et al., "Nanoindentation Studies on Shales," retrieved from URL <http://www.onepetro.org/download//conference-paper/ARMA-2013-578?id=conference-paper/ARMA-2013-578>, retrieved on Jul. 12, 2018, ARMA 13-578, American Rock Mechanics Association, presented at the 47th US Rock Mechanics/Geomechanics Symposium, Jun. 23-26, 2013, 10 pages.

Wang et al., "Characterization of electrical properties of organic-rich shales at nano/micro scales," Marine and Petroleum Geology, 86:563-572, Jun. 16, 2017, 10 pages.

* cited by examiner

FIG. 1

| Shale | Quartz | Albite | K-Feldspar | Mica-Ill-Smec | Chlorite | Kaolinite | Calcite | Dolomite | Siderite | Pyrite | Marcasite | Anatase | Apatite | Halite | Anhydrite | Gypsum | TOC (wt%) |
|---|---|---|---|---|---|---|---|---|---|---|---|---|---|---|---|---|---|
| 1 | 11 | 2 | 3 | 61 | 9 | 7 | 1 | 0 | 1 | 5 | 0.4 | 0.6 | 0.0 | 0.0 | 0.0 | 0.3 | 2.5 |
| 2 | 10 | 5 | 4 | 47 | 5 | 10 | 0 | 2 | 1 | 14 | 3.5 | 0.2 | 0.1 | 0.3 | 0.5 | 0.0 | 6.5 |

Table 1: Mineralogy and TOC data for each of the shale samples.

| Shale | S1 | S2 | S3 | PI | Tmax | TOC | HI | OI | H/C | Maturity |
|---|---|---|---|---|---|---|---|---|---|---|
| | mg/g | mg/g | mg/g | | C | wt% | | | | |
| 1 | 0.01 | 0.03 | 0.15 | 0.13 | 608 | 1.63 | 2 | 0 | | Post |
| 2 | 2.18 | 27.76 | 0.45 | 0.07 | 420 | 6.46 | 430 | 7 | 1.250 | Immature |

Table 2: Maturity data for each of the shale samples.

SYSTEM AND METHOD TO EVALUATE KEROGEN-RICH SHALE

TECHNICAL FIELD

This disclosure relates to kerogen and kerogen-rich shale.

BACKGROUND

Unconventional source rock are fine-grained, organic-rich sedimentary deposits such as shales and mud rocks. Although unconventional rock formations or reservoirs are porous composites, their pore sizes and permeability make the rock formations resistant to economical hydrocarbon flow. The permeability of the shale reservoir means that oil and gas typically are not economically produced from the well geometry, but rather through hydraulically fractured and stimulated wells.

Unconventional formations may include an organic material called kerogen intertwined with the rock matrix and the pores. Some unconventional formations can be characterized or labeled as a kerogen-rich shale (KRS).

Kerogen is a solid organic matter in sedimentary rocks. Kerogen is a natural organic biopolymer of irregular structure and thus typically not given a chemical formula. Kerogen composition can vary from reservoir to reservoir and from sample to sample within a given reservoir, and may be of different kerogen types. Kerogen can range in degree of saturation where the ratio of the aliphatic to aromatic content contributes to thermal maturity designations. Kerogen is insoluble in normal organic solvents because of the molecular weight of kerogen. Upon heating, kerogen may convert to liquid or gaseous hydrocarbons.

SUMMARY

An aspect relates to a method of evaluating kerogen-rich shale (KRS) including preparing a KRS sample. The method includes measuring, via scanning microscopy, the electrical conductivity of the KRS sample and a mechanical property of the KRS sample. The method includes correlating the electrical conductivity with a mechanical property among other shale physical characteristics.

Another aspect relates to a method of evaluating KRS including identifying, via spectroscopy, chemical components of a KRS sample. The method includes measuring, via atomic force microscopy (AFM), the electrical conductivity of the KRS sample and a mechanical property of the KRS sample. The electrical conductivity map has a resolution at the microscale or smaller. The method includes correlating spatially the electrical conductivity, the mechanical property, and the chemical components at micro- and nanoscales.

Yet another aspect relates to a system for KRS including a sample preparation system to polish a surface of a KRS sample. The system includes a spectrometer to identify chemical components of the KRS sample. The system includes an AFM instrument to measure electrical conductivity of the KRS sample and a mechanical property of the KRS sample. The electrical conductivity and mechanical property are each mapped in the same region. A computing system correlates spatially the electrical conductivity, the mechanical property, and the chemical components at microscale or smaller.

The details of one or more implementations are set forth in the accompanying drawings and the description to be presented. Other features and advantages will be apparent from the description and drawings, and from the claims.

DETAILED DESCRIPTION

The "high" resolution discussed in the present disclosure means micrometer scale or nanometer scale, or both. This disclosure relates to correlating resistivity well logs with microscale or nanoscale maps of kerogen and kerogen-rich shale electrical conductivity. The application may be kerogen, kerogen shale matrix, and kerogen rich shale (KRS) composite. An aspect of the disclosure is directed to mapping electrical conductivity (or resistivity) of KRS at the microscale and nanoscale.

The heterogeneous nature of KRS from source rock formations has proven challenging to characterize in the laboratory environment at macroscales and hence even more so in the subterranean scenario. Thus, embodiments of the present techniques include microscale or nanoscale analyses (for example, in the laboratory) for mapping the electrical conductivity of composite KRS at a microscale or nanoscale. These measurements may facilitate to establish the contribution of components of the composite KRS shale to the overall electrical conductivity of the composite KRS shale. These measurements may be associated with chemomechanical shale properties for correlation with field data obtained from seismicity or well logs. Upscaling can include correlating the measured conductivities with the porosity and the chemomechanical properties of KRS, and applying the measured conductivities to core and log data interpretation. Some embodiments of the present techniques may measure the conductivity of each source rock component, inorganic and organic, while linking this information to the mineralogy, porosity, lithology, thermal maturity, and domain orientation of the bulk KRS.

Certain embodiments capture the electrical conductivity of shales via atomic force microscopy (AFM). The AFM may obtain information about the electrical conductivities of source shale components including the minerals and organic matter. The information may be high resolution at the micrometer scale or nanometer scale. The conductivity may be relevant for resistivity log correlations of geological formations.

In implementations, the AFM can capture both the electrical and mechanical (elastic range) properties from the same location in the material. A reason to capture the mechanical properties in conjunction with the electrical characterization may be to identify the particular phases within the window of interest. Implementations provide for nanoscale electrical conductivity measurements and electrical conductivity mapping to relate (link) the electrical conductivity and mechanical properties to rock structure and resistivity logs. Embodiments apply high-resolution property mapping at the micrometer level or nanometer level in shales and consider electrical conductivity and mechanical properties.

Implementations utilize correlative testing that is innovative for evaluation of KRS. Such correlative analysis may include, for example, both material stiffness mapping via AFM and electrical conductivity mapping via AFM. The correlative analysis may include chemical identification via energy dispersive X-ray spectroscopy (EDS), AFM-infrared spectroscopy (AFM-IR), micro-Fourier-transform infrared spectroscopy (micro-FTIR), or fluorescence spectroscopy, or any combinations thereof. Further, the in-situ superposition method coupled with temperature effects may provide information about nanoscale characteristics.

The techniques may look beyond the electrical conductivity (and resistivity) of the inorganic components to electrical conductivity of the organic matter interbedded and interwoven within source shales, while coupling the electrical conductivity (or resistivity) property with mechanical and chemical characteristics. The organic matter (for example, kerogen, bitumen, and pyrobitumen) may alter electrical properties of KRS. As seen in this disclosure, the electrical conductivity of the organic matter is greater than the surrounding inorganic components, while the conductivity magnitude may depend upon the orientation of the bedding planes. Such can be a surprising result because the hydrocarbons (for example, gas and oil) in conventional reservoirs have shown less conductivity and greater resistivity than the rock itself. Embodiments beneficially incorporate the role of organic matter in the anisotropy of resistivity at microscale and nanoscale associated with the anisotropy of the mechanical properties according to bedding orientation. Upscaling and correlating this knowledge to field logs and seismicity provides an innovative technique for formation evaluation.

Resistivity logs have been employed for decades to capture the electrical properties of geological formations containing not only an array of different minerals but also fluid-filled pores. The resistance to electric current of the formation, including both the rock and the fluids, is generally proportional to the volumetric sum of the mineral grains and the fluid-filled pore space. In conventional reservoir rock, such as sandstone and carbonates, the pores (rock porosity) may be filled with varying amounts of gas, oil, and water that exhibit differences in resistance to electrical current due to changing saturation indices in the pore space. Reservoir formations containing more hydrocarbon than water in the collective pore space have greater bulk-formation resistance than when more water than hydrocarbon is present in the collective pore space.

In unconventional source rock formations, the analysis may be complicated due to the presence of organic matter such as kerogen and bitumen. Although the electrical properties of the individual source rock components have been measured on the bulk scale, electrical properties have not been previously isolated and quantified within the shale rock matrix. Capturing the electrical properties within the rock matrix benefits from the resolution of the AFM to isolate the micro-phase and nano-phase. The contributions of individual phases to the overall shale formation resistivity have not been well established in the past. Relating resistivity measurements in unconventional formations to changing kerogen maturity has generally not be feasible earlier in the art. The mechanical, chemical, and physical properties of kerogen can be different within and between different formations and can vary in composition according to diagenesis and kerogen thermogenic transformation (thermal maturity) into hydrocarbons. These phenomena can affect the electrical conductivity of the composite shale formation.

Kerogen maturity, structural embedment, porosities, and saturation with formation fluids could each play a role in magnitude and polarity of the electrical properties such as electrical conductivity. Maturity, for instance, may affect the conductivity because immature kerogen structures are associated with formations that are barely entering the oil window and which have a greater aliphatic content, while mature kerogen in gas wells is predominantly aromatic in nature. The graphitic nature of mature kerogen caused by depletion of hydrogen relative to carbon during burial results in the fusion of aromatic moieties within the kerogen. The subsequent alignment of these polar structures within the rock during this thermogenic process can enhance log-measured conductivities. Yet, at the same time, the competing effect of increasing porosity with maturity could counteract improvements (increases) in electrical conductivity that would otherwise be associated with greater maturity. Many factors may be at play in the complex kerogen-rich source shales that can have substantial effects upon the electrical properties of these materials leading to improper log interpretation for unconventional source rock formations.

In response, present embodiments capture the microelectrical and nanoelectrical conductivity of source-rock shale components including organics, clays, and minerals, while in-situ correlating at these same scales the chemomechanical properties of KRS for field upscaling. Certain embodiments employ AFM to map the electrical conductivity of source rock at the nanoscale and microscale, and in which this scale may be at the length scale of the individual components including the organic matter, clays, and minerals. The measured conductivities may be applied toward core and log data interpretation. In the case of both core and log data, the measured conductivity (or resistivity) may be representative of a large sample (for example, about 1-5 feet resolution for induction logs) for conventional rock where there is little or no heterogeneity of the rock matrix. For unconventional rock (for example, shale), however, the rock matrix that contains the organic components and pore space is typically heterogeneous with variations in the mix of clays and minerals that can affect the conductivity of the matrix. In addition, the changing aromaticity of the organic domains additionally can complicate interpretation of bulk measurements for these samples.

The AFM application employed here may provide several benefits for understanding electrical conductivity in unconventional rock such as KRS. Embodiments of these techniques of KRS characterization measure (for example, directly) the conductivity of source rock components, inorganic and organic, while linking this information to the mineralogy (for example, clay and mineral composition), lithology (for example, domain size and sorting), thermal maturity (for example, aromatic/aliphatic ratio), and domain orientation. This linking is generally not feasible with bulk practices. Embodiments may also systematically adjust the size of the mapped area. Therefore, the linking of the measured conductivity of various sized domains to that of the whole toward a framework for upscaling applications may be implemented.

In addition to characterizing dry samples at ambient temperature, AFM-based conductivity measurements can be performed with changing temperature and with fluid saturated samples. This may provide the ability to interrogate (for example, directly interrogate) samples at conditions that mimic log-measured conditions providing further understanding to develop nanoscale to log correlations. In particular, the percent expulsion of hydrocarbons from the more electrically-conductive organic domain may be determined in certain instances.

At nanometer resolutions, the conductivity maps in the organic domains can be used to understand the distribution of aromatic domains such as stacked or ordered regions. Such may provide information for modeling efforts to comprehend the chemical and structural changes of kerogen with thermal maturation leading to an understanding of pore structure and chemistry. Finally, in cases where KRS samples are of the same or similar thermal maturity and similar kerogen/bitumen ratios, the differences in electrical conductivity can be linked in some instances to differences in porosity at the AFM resolution.

In AFM measurements, the deflection of a weak cantilever of known spring constant versus tip-surface separation produces a set of force-distance curves that represent tip-sample interactions at each location on the sample. Regions of these curves may be utilized to measure or construe sample characteristics such as topography, adhesion, and mechanical properties. The AFM device may have different modes which can be selected and implemented sequentially or, in some cases, in parallel or contemporaneously. The modes may include a conductive or current mode in which electrical conductivity is measured. The modes may include a mechanical-property mode in which one or more mechanical properties are measured. The AFM device may also perform imaging or topographical imaging in which a topographical map (images) giving dimensions such as feature heights or elevations are obtained. Further, AFM device modes may be related to contact of the probe or tip to the sample, such as with continuous contact, intermittent contact, or no contact.

An AFM device from Bruker Corporation (headquartered in Billerica, Mass., USA) for conductivity measurements may have at least two AFM device modes: conductive AFM (C-AFM) and tunneling AFM (TUNA). These two modes may cover the range of conductivity from sub-nanoampere (nA) to microampere ($\mu$A) and sub-picoampere (pA) to nA, respectively. Differences in these modes, however, may go beyond the measurement range. For instance, C-AFM measurements, where the tip touches the surface, may be considered microscale characterization while the interactions measured in TUNA (proximity but non-contact) are considered atomic-scale in nature.

Electrical conductivity measurements may employ a conductive AFM device probe, an applied bias voltage across the sample, and a procedure to convert the measured current to a computer-readable signal. Both modes of operation (C-AFM and TUNA) may provide conductivity and topography maps of the sample surface via imaging or mechanical tapping performed by the AFM. The "imaging" discussed here may be electron imaging, optical imaging, light imaging, and other forms of microscopy that provide an image of the surface. When the AFM device is operated in intermittent contact, as with PeakForce TUNA™ (Bruker Corporation terminology), the conductivity map may be accompanied by an adhesion map and a modulus map allowing for direct comparison of the material differences with other mechanical properties at the nano- and micro-length scales. In addition, heat may be applied to the samples to observe (for example, directly observe) the effects on conductivity, adhesion, and modulus.

Figure 1:
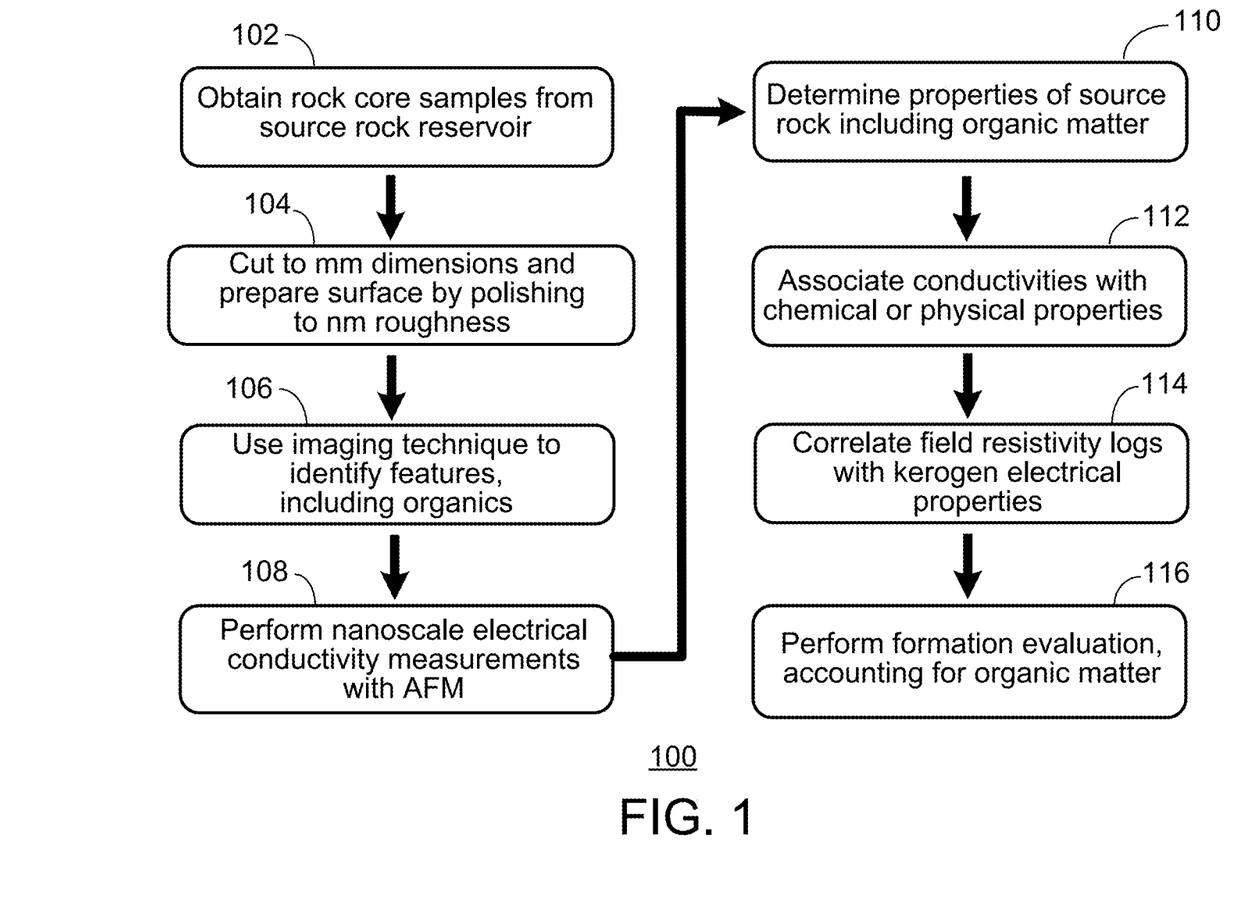
FIG. 1 is a block flow diagram of a method of evaluating kerogen-rich shale (KRS).

In summary, embodiments provide an innovative laboratory technique to capture shale electrical properties at the nanoscale and microscale, and then correlate the shale electrical properties with the mechanical and chemical characteristics of the composite KRS at these scales. FIG. 1 outlines exemplary actions implemented to capture mechanical, chemical, and physical properties and correlate the properties with electrical conductivity characteristics at the microscale and nanoscale. In some implementations, these correlations are utilized to upscale to logs and field data of source shale formations.

FIG. 1 is a method 100 of evaluating kerogen-rich shale (KRS). At block 102, the method includes obtaining a rock sample from source reservoir rock. In implementations, the method includes obtaining KRS samples from source reservoir rock and in which the KRS sample collected is a rock core sample or portions of a rock core sample. The source reservoir rock may be an unconventional source rock formation with presence of organic matter including kerogen, bitumen, and pyrobitumen.

At block 104, the method includes preparing the KRS sample for analyses. For instance, the KRS sample may be cut to millimeter (mm) dimensions. For example, the KRS sample can be cut to generally a cuboid shape (for example, FIG. 4) and with length, width, and height each a few millimeters or centimeters (cm). The length and width can each be, for example in the range of 1 mm to 80 mm, 3 mm to 60 mm, or 5 mm to 40 mm. The height can be, for example, in the range of less than 1 mm to 20 mm, 1 mm to 15 mm, or 1 mm to 10 mm. Instead of cuboid, the sample may be prepared generally cylindrical having a diameter and thickness each a few millimeters. The sample may also be prepared as an irregular shape but with a surface available for analysis.

Figure 4:
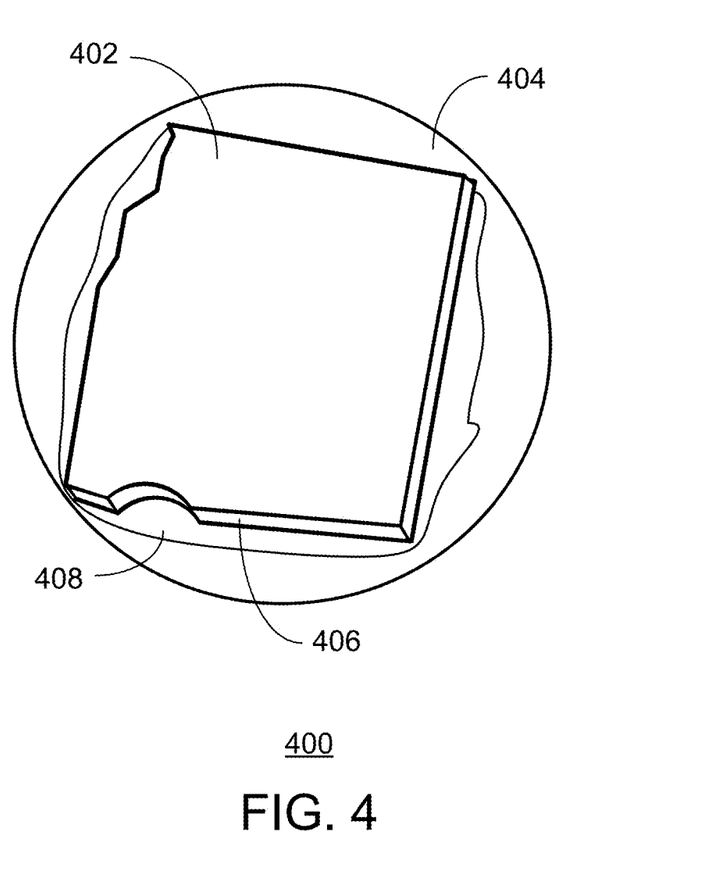
FIG. 4 is a diagrammatical representation of a KRS sample prepared for atomic force spectroscopy (AFM) testing.

In addition, a surface (for example, top surface) of the sample may be polished to a roughness in nanometers or micrometers. For instance, a top surface of the prepared sample similar or the same to that depicted in FIG. 4 is so polished. In implementations, the specified surface roughness is less than 15 $\mu$m, or in the ranges of 1 nm to 15 $\mu$m, 1 nm to 13 $\mu$m, or 1 nm to 10 $\mu$m. In certain embodiments, the sample surface may be polished mechanically and then finely polished via ion milling such as with an argon ion mill. In some implementations, the imaging and the AFM tapping mode may be performed on the polished surface. The EDS and AFM conductivity mode may be performed on the polished surface or on the volume of the sample, for example, through the sample.

At block 106, the method includes employing an imaging technique(s) to identify features of the KRS sample, including with respect to organics in the KRS sample. Imaging may be performed to determine porosity within the resolution limits of the imaging technique or instrument. Moreover, the method may include selecting a region of interest on the KRS sample, such as via imaging or microscopy, or both. A reason to select a region of interest may be to select a kerogen feature with a particular size, shape, maturity, or proximity to an inorganic feature. Another reason to select a region of interest is to have a point of reference for correlating the AFM measurement with other utilized techniques to directly compare the same region.

The method may include performing topographical imaging (for example, via the AFM) to confirm that the region of interest or sample area under examination or analysis is sufficiently smooth. Topographical imaging may be via the AFM tip moving along the sample surface. In contrast, optical imaging may be collected via a microscope. The optical image may be less resolution than topographical imaging but cover a larger area than topographical imaging. The topographical image may have same resolution as the other AFM properties and in the same region as the AFM analysis.

The method may include performing spectroscopy and imaging (for example, electron imaging, optical imaging, or light imaging) on the prepared sample (block 104) to identify chemical components spatially. The imaging may contribute to identifying components spatially such as by location. The components may include organic components and inorganic components. In certain embodiments, the spectroscopy is or includes EDS, AFM-IR, or micro-FTIR. The imaging may be performed by an AFM or other device. In certain implementations, the KRS sample (for example, sample fragments or material cut from the sample) may be milled and the powder subjected to x-ray diffraction (XRD) to identify components.

Rock-Eval® pyrolysis may be performed to interpret thermal maturity or other properties. Rock-Eval® pyrolysis was developed by Institut Français du Pétrole (IFP) (French Institute of Petroleum) based at Rueil-Malmaison, France. In such a pyrolysis analysis, a rock sample undergoes increasing temperature in an inert atmosphere where three peaks of released hydrocarbons can be measured. The first peak (S1) represents the volatilization of any previously generated hydrocarbons present in the rock, given that the rock has reached thermal maturity. The second peak (S2) indicates the thermal degradation of any remaining organic material into hydrocarbons. The final peak (S3) is any organic CO2 present in the rock. The temperature at which the S2 peak occurs may be an approximation of the thermal maturity of the rock. In addition to thermal maturation, pyrolysis peaks S1, S2, and S3 yield information about the type of organic material present in the rock. The type of organic material, or kerogen, may determine whether generated hydrocarbons will be oil (from sapropelic kerogen) or gas (from humic kerogen). Such may have economic implications. Sapropelic and humic kerogen can be broadly differentiated by the relation of the hydrogen and oxygen atomic ratios with respect to carbon. A greater oxygen-to-carbon ratio (O/C) or oxygen index is found in gas-yielding kerogens when compared to oil-yielding kerogens. This is related to the degree of anoxia present at the time of deposition. The ratios of S3/S1 peaks and S2/S1 peaks in the pyrolysis analysis are proxies for the kerogen oxygen index and kerogen hydrogen index, respectively.

At block 108, the method includes performing microscale or nanoscale electrical-conductivity measurements on the prepared sample with AFM or similar technique. An electrically conductive material such as a silver paste or electrically-conductive tape may be applied to the sides (or other surfaces) of the sample to provide a pathway for conduction of electrons from the sample surface to the base. The nanoprobe electrical-conductivity measurements may be conducted to map the electrical properties of the KRS samples. The electrical conductivity measurements may be performed with the AFM on the region of interest as selected in block 106.

The method may also include measuring porosity of the KRS sample, such as directly via the AFM instrument. The porosity may also be inferred or determined via the electrical conductivity measurements. The organic domains with developed porosity may show greater electrical conductivity than the inorganic regions. Changes in electrical conductivity may identify areas with porosity, including when the pore size is less than an imaging resolution limit. AFM conductivity maps around the pores can determine the distribution of graphitic domains around the pores and be utilized for modeling. Differences in electrical conductivity from samples of the same or similar thermal maturity may determine differences in porosity and organic matter type that may be less than the resolution of imaging.

Organic domains with generally no visible porosity are typically less electrical conductivity (for example, not visible in the conductivity map) than organic domains with visible porosity. The organic domains with developed porosity have greater electrical conductivity than organic domains with no visible porosity. This may be consistent with the expectation that areas where pores have developed are more graphitic and therefore would be more conductive. Such can aid in identifying areas of developed porosity when the pore size is less than the resolution limit for AFM and SEM imaging capabilities. An understanding of porosity may be a beneficial component of interpreting logs and predicting permeability. Some implementations apply AFM conductivity maps on fluid saturated samples to link to field logs.

At block 110, the method includes determining properties of the source rock including organic matter, such as via analysis of the KRS sample. The method can include performing mechanical tapping to obtain stiffness moduli or elastic moduli, and other mechanical or physical properties if desired. The mechanical mapping can be, for example, AFM mechanical tapping or two dimensional (2D) mechanical moduli mapping. Tapping mode may be labeled as dynamic contact mode, intermittent contact, or alternating current (AC) mode. In some implementations of AFM tapping mode, the cantilever is driven to oscillate up and down at or near the cantilever resonance frequency. A tapping AFM image may be produced by imaging the force of the intermittent contacts of the tip with the sample surface. In certain implementations, samples that contain regions of varying stiffness or with different adhesion properties can give a contrast via AFM not visible in the topographic image. Mechanical tapping may be performed with the Bruker AFM microscope instruments or devices such as via the Bruker AFM TappingMode™, PeakForce Tapping®, and quantitative nanomechanical mapping (QNM®).

At block 112, the method includes associating conductivities (for example, electrical conductivity measured in block 108) with chemical properties of the bulk KRS sample and with physical or mechanical properties of the bulk KRS sample, such as mineralogy, lithology, thermal maturity, rock structure, and domain orientation. Thus, embodiments directly measure (block 108) the electrical conductivity and measure (block 110) properties (for example, the stiffness modulus of source rock components, inorganic and organic), while linking (block 112) this information to the mineralogy (for example, clay and mineral composition), lithology (for example, domain size and sorting), thermal maturity (for example, aromatic/aliphatic ratio), domain orientation, and porosity differences. The linking to go from the electrical conductivity and stiffness modulus measured with the AFM to this list of properties may include spectroscopy and techniques such as EDS, Rock-Eval® pyrolysis, x-ray diffraction (XRD), and AFM-measured porosity. For this KRS characterization (block 112), the mapped electrical conductivity as measured and determined in block 108 may give chemical and mechanical characteristics of the KRS.

The method may include correlating the electrical conductivity with a chemistry map of the KRS sample to interpret effects of mineralogy and maturity. The chemistry map may be determined at least by spectroscopy. The chemistry map may be a map (locations) of chemical components of the KRS sample. The map may include concentrations, such as weight percent, of the chemical components.

At block 114, the method includes correlating field resistivity logs with kerogen electrical properties (for example, electrical conductivity). The method can include identifying and correlating the chemical and mechanical properties to field data. The chemical and mechanical properties may be those addressed in blocks 110 and 112. The field data may be seismicity logs, well logs, and resistivity logs. The electrical conductivity may be relevant for resistivity log correlations of geological formations.

Upscaling can include correlating the measured conductivities with the chemomechanical and geomechanical properties of KRS and applying the measured conductivities to core and log data interpretation. The method may include upscaling the electrical conductivity as measured and the mechanical property as measured to field data of a KRS geological formation from which the KRS sample was obtained. For instance, the upscaling may include correlating or linking the electrical conductivity (for example, nanoscale electrical conductivity measurements) to resistivity logs of a KRS source formation. The correlating can mean comparing, calibrating, and developing correlations or equations.

In a particular implementation, the measured electrical conductivity in the 2D image provided 10 nm resolution electrical conductivity parameters. Averaging and other techniques can determine the upscaled electrical conductivity at the length scale of the full 2D map. By collecting multiple 2D maps, statistics can be provided at this level. Collecting multiple adjacent maps, the 2D estimate can be increased by an order of magnitude to the millimeter scale. In this particular implementation with these data, digital rock approaches can be employed to estimate the three dimensional (3D) microscale and core scale data (approximate resolution of 3 feet) that is generally the resolution of the resistivity log.

At block 116, the method includes performing formation evaluation including accounting for organic matter. The formation can be the geological formation from which the KRS sample material was obtained. The method can include correlating the tested chemical, mechanical, and electrical properties of the KRS sample to log and seismic information of a KRS formation to evaluate the KRS formation including organics. The method may include upscaling the electrical conductivity as measured to field data of a KRS source formation from which the KRS sample was collected.

EXAMPLES

Two KRS (shale) samples were prepared for AFM testing. Each sample was cut to millimeter (mm) dimensions, mounted to a conductive metal stub, polished mechanically, and finely polished with an argon ion mill. Mechanical measurements were then performed, including 2D mechanical moduli mapping, to identify the spatial distribution of the various KRS components. In lieu of EDS data, the 2D mechanical moduli mapping was used to qualitatively distinguish the organic rock components from the inorganic rock components. Modulus mapping may map elastic modulus and other mechanical properties of a material surface at nanoscale.

Next, silver paste was applied to the sides of the samples to provide a pathway for conduction of electrons from the sample surface to the base. Nanoprobe electrical-conductivity measurements were conducted to map the electrical conductivity of the KRS samples The bulk properties (for example, mineralogy and thermal maturity) of the two shale samples were characterized in order to define any variation in the material properties. Each sample was milled with a Retsch™ Mixer Mill MM400 to obtain a powder. The powder was analyzed via XRD with a Bruker D8 Advance Eco powder diffractometer and then analyzed using Rietveld refinement to determine the mineral constituents. Rietveld refinement characterizes crystalline materials in that neutron and x-ray diffraction of powder samples results in a pattern characterized by reflections (peaks in intensity) at certain positions. The mineralogy of each sample is shown in table 200 (Table 1) in FIG. 2.

Figure 2:
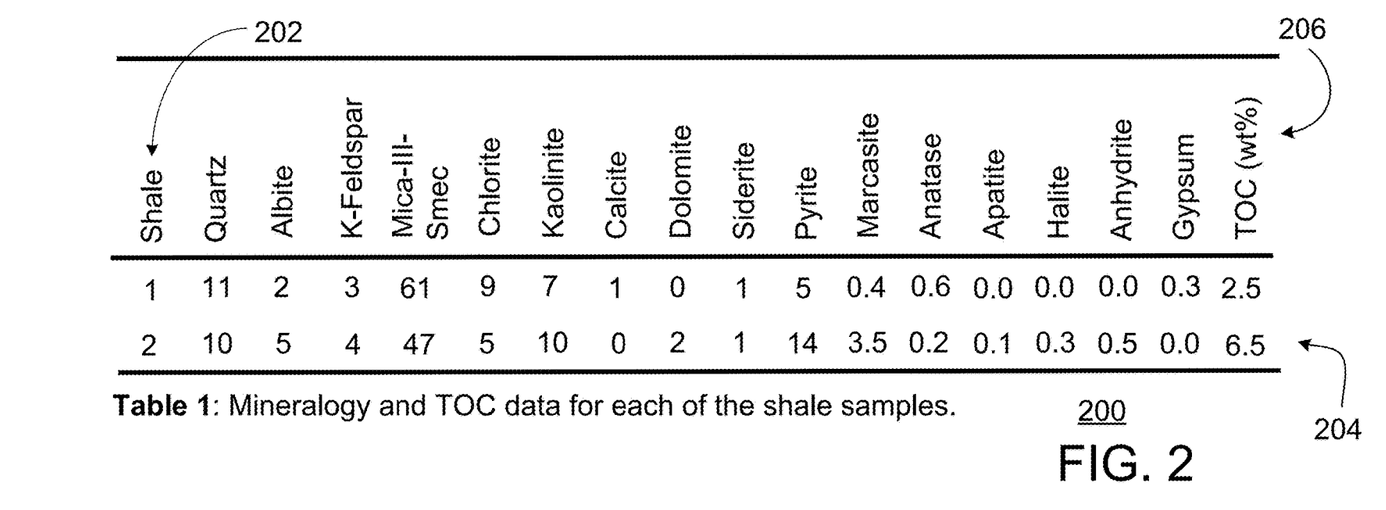
FIG. 2 is a diagram tabulating mineralogy and total organic content (TOC) data for each of two shale samples that are KRS samples.

FIG. 2 is a table 200 depicted as "Table 1. Mineralogy and TOC data for each of the shale samples." The two shale samples which are KRS samples and are labeled as shale sample 1 and shale sample 2, as indicated by reference numeral 202. The table gives values 204 in weight percent for total organic content (TOC) and chemical components 206.

Rock-Eval® pyrolysis was utilized to determine the percent weight of organic matter as well as delineate the amount of each organic matter component and the overall maturity of the rock sample. Crushed rock samples (about 60 milligrams or mg) were subjected to a programmed temperature where the organic matter thermally decomposed over time and the resulting by-products of this decomposition were measured via a flame ionization detector. During the pyrolysis analysis, a maximum temperature (Tmax) of complete combustion was reached and a pyrogram produced that recorded the hydrocarbon generative potential of the kerogen, both of which can be utilized to define the maturity. This procedure lost track of the spatial organic connectivity to the overall mineral and multi-porosity KRS structures.

Figure 3:
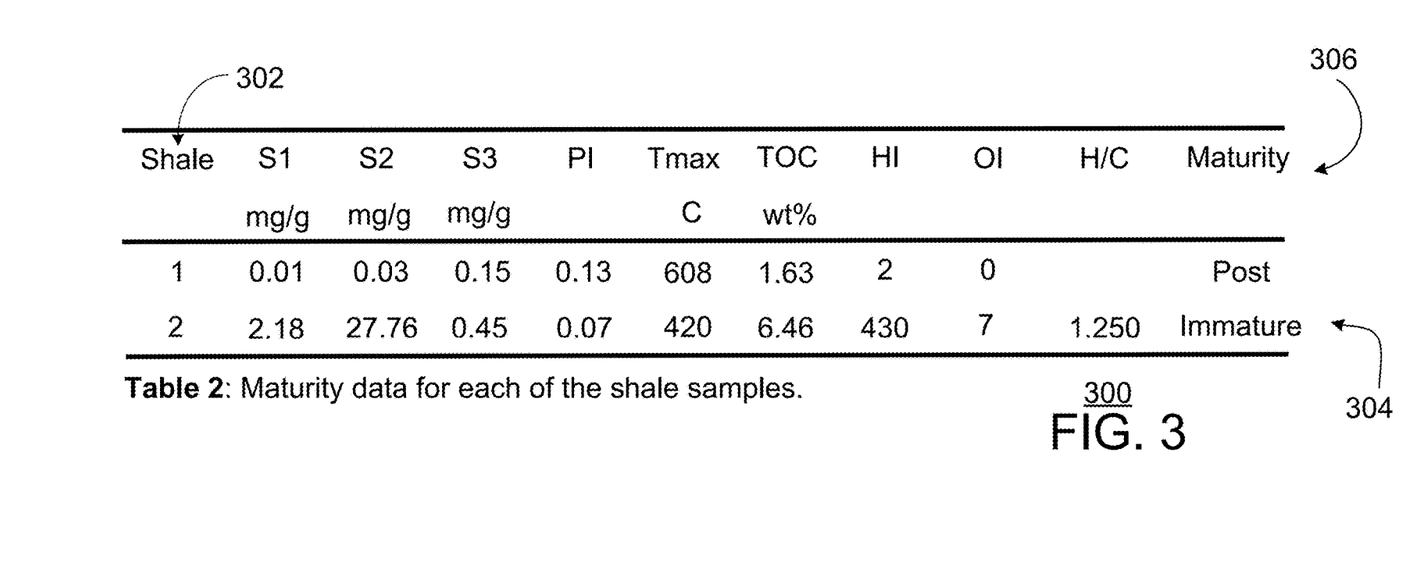
FIG. 3 is a diagram tabulating maturity data for each of the two KRS samples of FIG. 2.

FIG. 3 is table 300 depicted as "Table 2. Maturity data for each of the shale samples." The two shale samples are shale sample 1 and shale sample 2, as indicated by reference numeral 302. The table gives values 304 for properties 306. The properties 306 are S1 (milligram per gram or mg/g), S2 (mg/g), S3 in (mg/g), (productivity index), Tmax (° C.), HI (hydrogen index), OI (oxygen index), and H/C (hydrogen to carbon ratio), and maturity. S1, S2, and S3 are pyrolysis peaks. S1 is free hydrocarbons present in the sample before the analysis. S2 is the amount of hydrocarbons that formed during thermal pyrolysis of the sample (utilized to estimate the remaining hydrocarbon-generating potential of the sample). S3 is the $CO_2$ yield during thermal breakdown of kerogen.

Nanoscale electrical-conductivity measurements were performed with a Bruker Dimension Icon AFM instrument using the PeakForce TUNA™ module (operating mode). Further, tapping mode was employed to simultaneously collect conductivity, modulus, adhesion, dissipation, and deformation data at each imaging pixel. AFM Tapping-Mode™ is a Bruker technique that maps topography by tapping the surface with an oscillating probe tip and in which the oscillation amplitude of the cantilever changes with sample surface topography, and the topography image obtained by monitoring these changes.

FIG. 4 is a general representation 400 of a shale sample 402 prepared for AFM testing, such as with shale sample 1 and shale sample 2. The top surface is polished. In the depicted implementation, the sample 402 is fixed to a sample holder 404. The sample 402 has a thickness 406. In the illustrated embodiment, a silver paste 408 is deposited in selected locations around the perimeter of the sample.

Example 1

KRS sample 1 having dimensions of approximately 10 mm×10 mm×2 mm was prepared for AFM testing. The sample was oriented with shale bedding planes exposed to the surface, while the applied electrical conductivity path was parallel to bedding. Employing an optical microscope of the AFM, an area of the shale sample selected was expected to have both inorganic and organic components.

Figure 5:
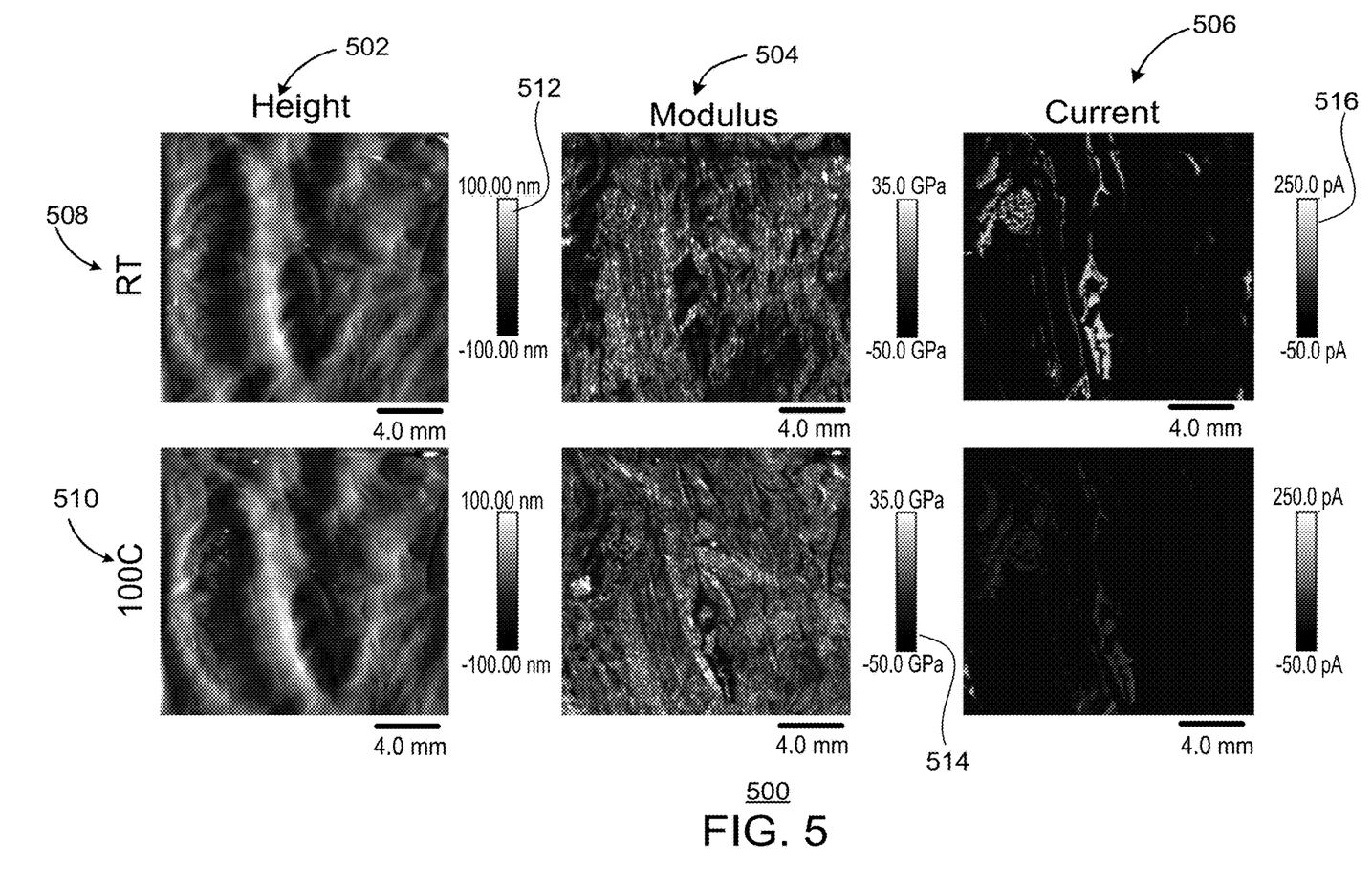
FIG. 5 is a diagram of images associated with the analyses of first KRS sample of FIGS. 2-3.

FIG. 5 are images 500 associated with the analyses of KRS sample 1. Two topography (height) image maps 502 on the left, two modulus image maps 504 in the center, and current image maps 506 (right) for shale sample 1 are given, respectively, at room temperature 508 (top) and temperature 510 of 100° C. (bottom). The shading of the elevation or height legend 512 represents nanometers (nm). The shading of the modulus legend 514 represents gigapascals (GPa). The shading of the current legend 516 represents picoamps (pA).

Topographical imaging (left 502) and PeakForce Quantitative Nanomechanical Mapping (PF-QNM®) were both performed (simultaneously with the AFM). Topographical imaging confirmed that the sample area under examination or analysis is sufficiently smooth (for example, surface roughness less than 1 mm). Topographical imaging was via the AFM tip moving along the sample surface. Optical imaging was collected using the microscope on the instrument. The optical image was less resolution than the topographical image but covered the entire sample surface. The topographical image was a region in the optical image. The topographical image had the same resolution as the other AFM properties and in the same region of sample surface as the AFM analysis.

The topographical imaging gave elevation changes (the height of features) on the analyzed surface of the sample. The QNM® gave mechanical properties. FIG. 5 (center 504) shows the modulus maps obtained at both room temperature and 100° C. The range of moduli differ for various source rock components. In general, the organic components exhibited moduli two or three times less than clays which are approximately two to three times more compliant than quartz and calcite. Areas exhibiting the least elastic moduli represent the organic domains where variations in moduli may be related to organic matter type (for example, kerogen, bitumen, and pyrobitumen) and porosity. In these noisy data, some qualitative observations can be made about how modulus changes with temperature. Subtle decreases (for example, less than 10%) in moduli in the inorganic domains were observed upon heating the sample whereas in the organic domains the modulus remained similar or slightly increased (for example, less than 10%).

Electrical conductivity measurements were also performed in the same area. FIG. 5 (right 506) displays the current maps that were captured at room temperature and 100° C. with the same applied bias. The organic domains with developed porosity showed greater electrical conductivity than the inorganic regions. A pyrite framboid (FIG. 5 upper left corner at 502, 508) displays comparable levels of conductivity to the kerogen. In fact, close inspection of the framboid suggested that the greater electrical conductivity is associated with the organic domains between the pyrite crystals and not the pyrite itself. Conductivity across the sample decreases upon raising the temperature to 100° C. that could be due to water evaporation at the micropores and nanopores. Some grains or clusters of grains within the testing window decreased in conductivity more than others. Organic domains with generally no visible porosity had less electrical conductivity (not visible in the conductivity map). The organic domains with developed porosity (visible porosity) are greater in electrical conductivity than organic domains with no visible porosity. This is consistent with the expectation that areas where pores have developed are more graphitic and therefore would be more conductive. Such can aid in identifying areas of developed porosity when the pore size is less than the resolution limit for AFM and scanning electron microscope (SEM) imaging capabilities. An understanding of the porosity may be a beneficial component of interpreting logs and predicting permeability.

Example 2

KRS sample 2 with dimensions of approximate 10 mm×10 mm×2 mm was prepared for AFM testing. The sample was oriented with shale bedding planes exposed to the surface while electrical conductivity perpendicular to the bedding. Employing an optical microscope and EDS, an area of the shale sample expected to have both inorganic and organic components was selected for testing.

Figure 6:
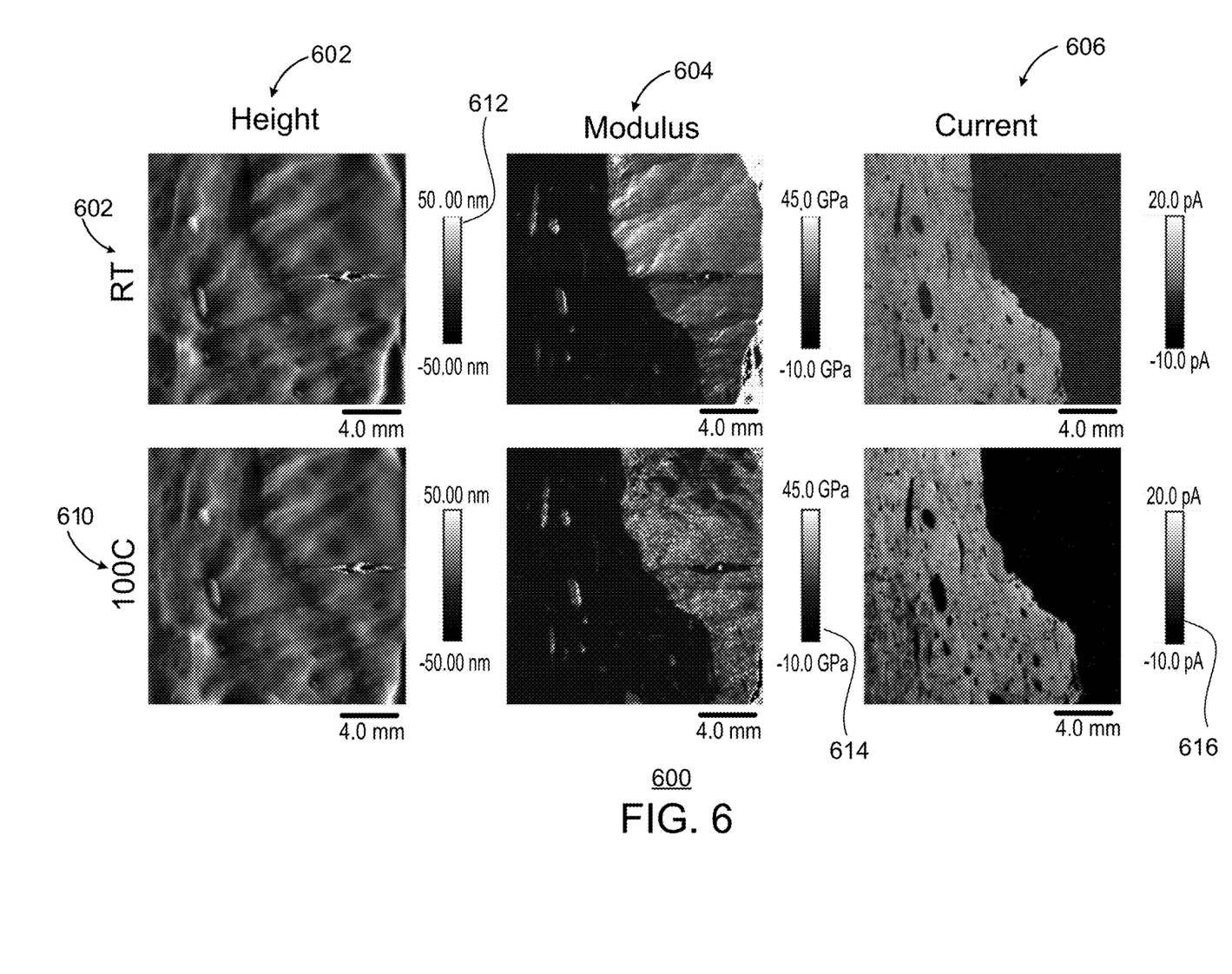
FIG. 6 is a diagram of images associated with the analyses of second KRS sample of FIGS. 2-3.

FIG. 6 are images 600 associated with the analyses of KRS sample 2. Two topography (height) maps 602 on the left, two modulus maps 604 in the center, and current maps 606 (right) for shale sample 2 are given, respectively, at room temperature 608 (top) and temperature 610 of 100° C. (bottom). The shading of the elevation or height legend 612 represents nanometers (nm). The shading of the modulus legend 614 represents gigapascals (GPa). The shading of the current legend 616 represents picoamps (pA).

Topographical imaging (left 502) and quantitative nanomechanical mapping (QNM®) were both performed. FIG. 6 (center 604) shows the QNMs obtained at both room temperature and 100° C. The large dark region on the left portion in the two center 604 images exhibits less elastic moduli and represents an organic feature. Slight elastic moduli decreases (for example, decreases less than 10%) were observed upon heating the sample.

Electrical conductivity measurements were also performed in the same area. FIG. 6 (right 606) displays the maps that were captured at room temperature and 100° C. The organic region on the left portion of these two maps 606 is more electrically conductive than the region on the right portion in these two maps 606. Further, the kerogen appeared to have sub-domains where variations in electrical conductivity are noted. Such may suggest differences in the chemical or physical properties of the organic matter within this sample. Upon heating, the conductivity decreased slightly (less than 10% decrease) with most notable changes taking place in the inorganic domain (on the right portion of the two 606 images). This observation correlates with mechanical properties and also depending on the KRS organic and non-organic structural orientations.

Here, the cantilevers were not fully calibrated so quantitative observations are approximate. However, for a fully calibrated cantilever, the observed conductivity differences between sample 1 and sample 2 can be used for comparison. For instance, the conductivity of sample 1 (post mature) is greater than sample 2 (immature), which is consistent with the thermal maturity differences.

In summary, embodiments include high-resolution property mapping (micrometer or nanometer scales, or both) in shales such as KRS and consider electrical conductivity of the shales. Certain embodiments employ AFM to capture the electrical conductivity of shales such as of a KRS sample in the laboratory or field unit. The AFM may obtain high resolution information about the electrical conductivities of source shale components including the minerals, pore space, and the organic matter. The electrical conductivity may be relevant for resistivity log correlations of geological formations. In some embodiments, the AFM captures both electrical and mechanical (elastic range) properties from the same location in the shale sample material. A reason to capture the mechanical properties in conjunction with the electrical properties (for example, electrical conductivity) and porosity is to identify the particular phases within the window of interest. Nanoscale electrical conductivity measurements or electrical conductivity mapping may relate the electrical and mechanical properties to rock structure, and be linked to resistivity logs.

Some embodiments associate electrical conductivities of organic matter with a specific physical or chemical property and correlate with field resistivity logs in order to improve formation evaluations. Mineralogical, total organic carbon, and maturity parameters of shale (KRS) samples from relevant depths, and collated data accordingly for correlative analyses, may be utilized. Certain embodiments map electrical conductivities of mobile hydrocarbons and immobile kerogen to track the percent expulsion of hydrocarbons from the source rock. Implementations provide for electrical conductivity correlations to the kerogen geomechanics characteristics associated with the chemomechanics of KRS including in space, age, or maturity, or any combinations thereof.

Some embodiments accommodate AFM equipment, AFM data collection, and AFM interpretation. Some implementations apply AFM conductivity maps on fluid saturated samples to link to logs. Changes in electrical conductivity identify areas with porosity such as when the pore size is less than an imaging resolution limit. AFM conductivity maps around the pores can determine the distribution of graphitic domains around the pores including for modeling. Differences in electrical conductivity from samples of the same thermal maturity determine differences in porosity and organic matter type that may be less than the resolution of imaging.

Considered may at least be: (1) geochemistry concerning the chemical structure of kerogen and how the electrical conductivity changes with increasing aromaticity; (2) how the electric conductivity as related to dielectric response can be related to maturity which may be a measure of kerogen's transformation into hydrocarbons; and (3) application of AFM for characterization of the properties of kerogen. Conductive AFM as utilized here is a tool for revealing the morphology on the nanoscale and detecting the electrical conductivity on the same location for direct correlation between morphology and electrical conductivity.

Figure 7:
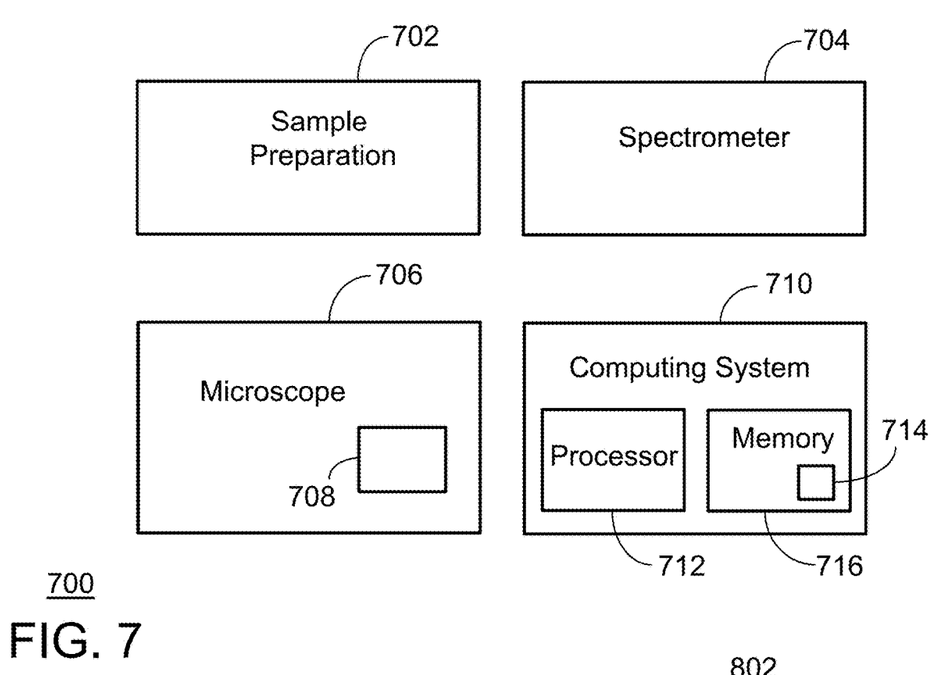
FIG. 7 is a diagram of a KRS evaluation system to analyze a KRS sample and correlate sample analyses to the KRS source formation.

FIG. 7 is a KRS evaluation system 700 to analyze a KRS sample and correlate sample analyses to the KRS source formation. The KRS source formation may be a KRS geological formation characterized as an unconventional formation. The KRS source formation may have hydrocarbons such as crude oil and natural gas.

A sample preparation system 702 may receive KRS material from the KRS source formation. The sample preparation system 702 may include tool(s) to cut or otherwise shape the KRS material into a KRS sample for analysis. In addition, the preparation system 702 may include refining devices to polish one or more surfaces of the KRS sample. For instance, a mechanical polisher may provide for gross or coarse polishing of the KRS sample surface, and an ion mill (for example, argon ion mill) may provide for fine polishing the KRS sample surface. In particular implementations, the surface may be polished to a specified surface roughness, such as in a range of 1 nm (or less) to 13 µm. In some implementations, a top surface of the KRS sample is polished for receipt of (or interaction by) a microscopic probe and for imaging.

To prepare the KRS sample to be subjected to electrical conductivity measurements (for example, via AFM such as C-AFM or TUNA), the sample preparation system 702 may include and apply electrically conductive material to the KRS sample. For instance, the electrically conductive material can be tape or a paste (for example, silver paste) applied to the KRS sample, such as around a perimeter of the sample. See FIG. 4 for an implementation of a prepared KRS sample.

In the illustrated embodiment, the KRS evaluation system 700 includes a spectrometer 704 system to analyze the KRS sample including the prepared KRS sample. The spectrometer 704 system may measure or identify chemical components or constituents of the KRS sample, such as organic compounds (for example, kerogen and bitumen) and inorganic compounds (for example, rock, minerals, and clay). In certain implementations, the spectrometer 704 system is an EDS instrument or device and having circuitry (including a hardware processor and memory) and a user-interface. In some implementations, the spectrometer 704 may be at least one of an AFM-infrared red spectroscopy (AFM-IR) instrument, a micro-Fourier-transform infrared spectroscopy (micro-FTIR) instrument, or a fluorescence spectroscopy instrument. Moreover, imaging of the KRS sample may be performed, for example, via a microscope associated with or separate from the spectrometer 704 system. Such microscopic imaging may facilitate identifying the chemical components spatially on the KRS sample, including at the microscale or nanoscale.

The KRS evaluation system 700 includes a microscope 706 system which may employ scanning microscopy to analyze the KRS sample at the microscale or nanoscale. The microscope 706 system may employ scanning probe microscopy including atomic force microscopy (AFM). In some implementations, the microscope 706 system may analyze and image the polished surface of the prepared AFM sample.

If AFM is employed, the AFM may include conductive AFM to measure electrical conductivity and AFM tapping or similar feature to measure a mechanical property, and other forms of AFM implementation. An AFM device or instrument as the microscope system 706 system may include circuitry 708 that provides for a user interface and for selection of different operating modes of the AFM system. Exemplary operating modes include conductive AFM (for example, C-AFM) to measure electrical conductivity and an AFM mechanical-property operating mode (for example, mechanical tapping) to measure elastic modulus and other mechanical properties.

In certain embodiments, the microscope 706 system may perform microscopic imaging on the KRS sample at microscale or nanoscale, such as on the polished surface of the KRS sample. In some embodiments, this imaging (for example, optical imaging) may be performed contemporaneous with the microscope 706 system measuring electrical conductivity or measuring the mechanical property. Imaging (for example, optical microscopic imaging) may facilitate correlating (for example, matching and linking) spatially the measured electrical conductivity with the measured mechanical property at the corresponding locations including on the microscale or nanoscale. Similarly, imaging (as associated with the spectrometer 704 system) may facilitate identifying the chemical components spatially including at the microscale or nanoscale. In some implementations, the circuitry 708 may include a hardware processor and memory storing code executed by the processor to correlate or location-match the electrical conductivity, mechanical property, and the chemical components.

The KRS evaluation system 700 may also include a computing system 710 to perform the aforementioned correlating or location-matching. The computing system 710 has a processor 712 and memory 714 storing code 716 (for example, logic and instructions) executed by the processor 712 to perform such location-matching, as well as other correlating and upscaling such as with respect to the KRS source formation as discussed in the present disclosure. The computing system 710 may be single computing device or a computer, a server, a desktop, a laptop, multiple computing devices or nodes, a distributed computing system, or control system. The computing system 710 may be local (for example, in the laboratory) or remote from the spectrometer system 704 and microscope 706 system. The computing system 710 may represent multiple computing systems or devices across separate geographical locations. The computing system 710 may be a component of a control system. The processor 712 may be one or more processors, and each processor may have one or more cores. The hardware processor(s) 712 may include a microprocessor, a central processing unit (CPU), graphic processing unit (GPU), or control card. The memory 714 may include volatile memory (for example, cache and random access memory or RAM), nonvolatile memory (for example, hard drive, solid-state drive, and read-only memory or ROM), and firmware.

In operation, the computing system 710 may link the electrical conductivity, the mechanical property, and the chemical components (and porosity) as spatially correlated to mineralogy, lithology, thermal maturity, and domain orientation of bulk KRS. The bulk KRS may be the bulk KRS of the KRS sample or bulk KRS of a source formation from which the KRS sample was collected. The computing system 710 may upscale the electrical conductivity as measured and the mechanical property as measured to field data of a KRS source formation from which the KRS sample was collected.

The computing system 710 is unconventional, for example, in that the computer correlates microscopic analysis of a KRS sample with properties of the KRS geological source formation. In this context, the computer is innovative with respect to feasibility and accuracy. The technology of geological formation evaluation (including evaluation of unconventional formations of KRS) is improved. The computing system 710 provides for improved placement of wells in strategic locations in unconventional formations and thus increased production (more economic production) of hydrocarbon (for example, crude oil and natural gas) for a well.

Figure 8:
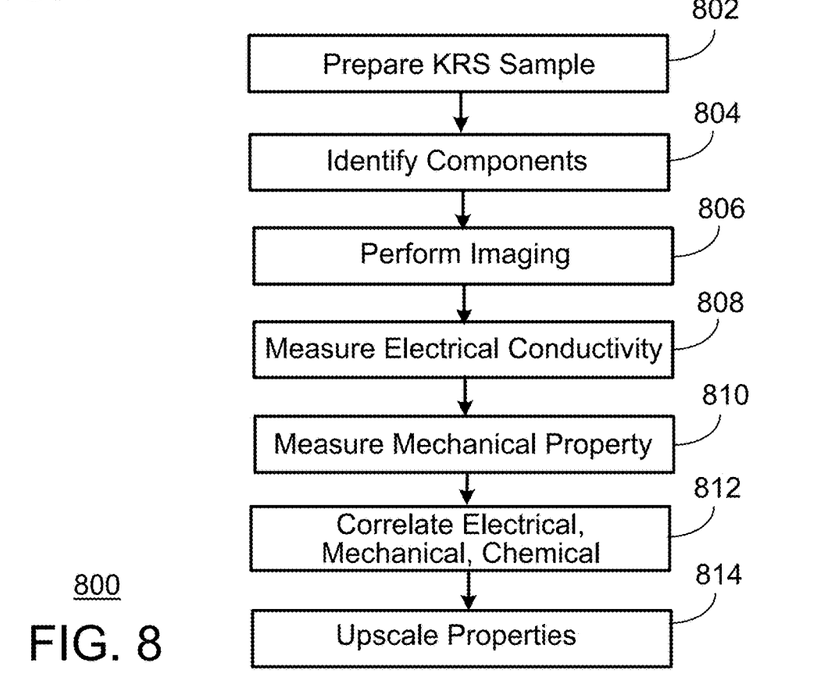
FIG. 8 is a block flow diagram of a method of evaluating KRS.

FIG. 8 is a method 800 of evaluating KRS, such as analyzing and evaluating a KRS sample (for example, prepared from sample material of a KRS source formation) and evaluating the KRS source formation correlative with the KRS sample analyses. At block 802, the method includes preparing the KRS sample. The sample preparation may include forming (for example, cutting or shaping) the KRS sample from a sample of a KRS geological formation and polishing a surface (for example, top surface) of the KRS sample. If polishing is employed, the polishing may include mechanically polishing and ion milling (for example, argon ion milling) the surface to a specified surface roughness. In one implementation, the specified surface roughness is in a range of 1 nm to 13 µm. In another implementation, the surface roughness in less than 15 µm.

The sample preparation may also include applying an electrically conductive material (for example, paste or tape) to a portion of the KRS sample, such as around a perimeter of the KRS sample. This application of an electrically conductive material may be to facilitate measurements of electrical conductivity of the KRS sample.

At block 804, the method includes identifying chemical components of the KRS sample such as via a spectrometer system. If a spectrometer system is employed, the spectrometer system in some embodiments is an EDS instrument or device, as discussed previously. The chemical-component measurements may also be via AFM-IR, micro-FTIR, fluorescence spectrometer, or other measurement techniques that can capture chemical information at spatial resolution in the micrometer to nanometer scales. The components identified may be organic and inorganic. The components may be identified spatially (for example, at the microscale or nanoscale) on the analyzed surface of the KRS sample. Such spatial or location recognition may be performed with the aid, for instance, of imaging performed in block 806 or other imaging such as topographic map imaging. The method may generate a chemistry map by at least spectroscopy. The chemistry map may be a map (locations) of chemical components of the KRS sample. The map may include concentrations, such as weight percent, of the chemical components.

The method may include performing Rock-Eval® pyrolysis to interpret thermal maturity or other properties. The pyrolysis may be the decomposition of organic matter by heating in the absence of oxygen. The pyrolysis may be employed to measure richness and maturity of potential source rocks. In a pyrolysis analysis, the organic content may be pyrolyzed in the absence of oxygen, then combusted. The amount of hydrocarbons and carbon dioxide released may be measured. A pyrolysis technique is Rock-Eval®. In Rock-Eval® pyrolysis, a sample may be placed in a vessel and progressively heated (for example, to 550° C.) under an inert atmosphere. During the analysis, the hydrocarbons already present in the sample are volatized and the amount of these hydrocarbons measured and recorded as a peak known as S1. Next, the amount of hydrocarbons generated by pyrolysis of kerogen in the sample is recorded as an S2 peak. The amount of $CO_2$ generated is recorded as the S3 peak. The amount of residual carbon is measured and recorded as S4. The percent total organic carbon (TOC) may be related to the S peaks.

At block 806, the method includes performing imaging of the KRS sample such as optical microscope imaging, electron imaging, or light imaging of the polished surface of the KRS sample at the microscale or nanoscale, or both. The imaging may be microscopy imaging performed via scanning microscopy and performed contemporaneous with measuring the electrical conductivity or with measuring the mechanical property, as in blocks 808 and 810, respectively. Thus, as in block 812 to be presented, the imaging may facilitate associating spatially the electrical conductivity, the mechanical property, and identified chemical components. Again, chemical components of the KRS sample may be identified spatially via the spectroscopy and the imaging.

The method may include selecting a region of interest on the KRS sample, such as via imaging or a microscope. The region of interest may be selected for evaluation or analysis. The method may also include performing topographical imaging (for example, via the AFM) to confirm that the region of interest or sample area under examination is adequately smooth (for example, a surface roughness less than 14 μm).

At block 808, the method includes measuring electrical conductivity of the KRS sample such as via scanning microscopy including scanning probe microscopy or AFM. The measuring of the electrical conductivity may involve mapping the electrical conductivity at microscale or nanoscale, or both. In certain embodiments, the measuring of electrical conductivity may include measuring the electrical conductivity via AFM such as with an AFM instrument in a specified operating mode (for example, conductive mode or current mode). The measuring of the electrical conductivity may include mapping the electrical conductivity so to relate the electrical conductivity and the mechanical property (block 810) to rock structure of the KRS sample.

The method may also include measuring porosity of the KRS sample, such as directly via the AFM instrument. The porosity may also be inferred or determined via the electrical conductivity measurements. In cases where KRS samples are of the same or similar thermal maturity and similar kerogen/bitumen ratios, the differences in electrical conductivity can be linked, in some instances, to differences in porosity, including when the porosity is outside of the resolution limits of instrument techniques. The organic domains with developed porosity may show greater electrical conductivity than the inorganic regions or organic regions with no visible porosity. Changes in electrical conductivity may identify areas with porosity, including as mentioned when the pore size is less than an imaging resolution limit. AFM conductivity maps around the pores can determine the distribution of graphitic domains around the pores including for modeling. Differences in electrical conductivity from samples of the same or similar thermal maturity may determine differences in porosity and organic matter type that may be less than the resolution of imaging.

Organic domains with generally no visible porosity are typically less electrical conductivity (for example, not visible in the conductivity map). The organic domains with developed porosity show greater electrical conductivity than organic domains with no visible porosity. This may be consistent with the expectation that areas where pores have developed are more graphitic and therefore would be more electrically conductive. Such can aid in identifying areas of developed porosity when the pore size is less than the resolution limit for AFM and SEM imaging capabilities. An understanding of porosity may be a beneficial component of interpreting logs and predicting permeability. Some implementations apply AFM conductivity maps on fluid saturated samples to link to field logs.

At block 810, the method includes measuring a mechanical property (for example, stiffness modulus and elastic modulus) of the KRS sample such as via scanning microscopy including scanning probe microscopy or AFM. In embodiments, the scanning microscopy may involve tapping (for example, mechanical tapping and modulus tapping) to measure the mechanical property. The scanning microscopy may measure the mechanical property on the polished surface of the KRS sample. The measuring of the mechanical property via the AFM may be in a specified operating mode (for example, tapping and QNM®) of the AFM microscope instrument. The measuring may include measuring the mechanical property and the electrical conductivity (block 808) at same locations in or on the KRS sample.

At block 812, the method includes correlating (for example, spatially) the electrical conductivity, the mechanical property, and the chemical components on the KRS sample. The method may include porosity in the spatial correlation. As mentioned, the chemical components may be organic and inorganic (for example, minerals). The method may include evaluating a KRS source formation based at least in part on this correlating of these properties of the KRS sample with each other. The correlating may include correlating the electrical conductivity with the mechanical property (and with the chemical components) at the same locations. The correlating may include matching electrical conductivity with the mechanical property (and chemical components) at specific locations on the KRS sample at microscale or smaller, for example, less than one millimeter. The method may include correlating the electrical conductivity with a chemistry map of the KRS sample to interpret effects of mineralogy and maturity A particular embodiment of blocks 802-812 collectively involves a method of evaluating KRS including: (1) preparing a KRS sample and identifying, via a spectrometer (for example, EDS instrument), chemical components of the KRS sample; and (2) measuring, via AFM, electrical conductivity of the KRS sample and a mechanical property of the KRS sample. The measuring of electrical conductivity may include mapping the electrical conductivity at microscale or smaller. The electrical conductivity, the mechanical property, and the chemical components (and porosity) of the KRS sample may be correlated with each other spatially at microscale or smaller.

At block 814, the method includes upscaling the properties. The method may include upscaling the electrical conductivity as measured to field data of a KRS source formation from which the KRS sample was collected. The method may include upscaling the electrical conductivity as measured and the mechanical property as measured to field data of a KRS geological formation from which the KRS sample was obtained. For instance, the upscaling may include correlating or linking the electrical conductivity (for example, nanoscale electrical conductivity measurements) to resistivity logs of a KRS source formation. In another implementation, the upscaling includes linking the electrical conductivity of the chemical components with at least one of mineralogy, lithology, thermal maturity, or domain orientation of bulk KRS. The bulk KRS may be bulk KRS of the KRS sample or bulk KRS of a source formation from which the KRS sample was collected.

Measurement results of electrical, chemical, physical, and mechanical properties (and porosity) at the same location on a KRS sample can be correlated (upscaling) to field data (for example, resistivity) or bulk properties. The correlations with upscaling may be performed by a computer with innovative code having logic and instructions developed for the data collected in addition to data at longer length scales (for example, length greater than 2 feet). In one implementation, the upscaling includes correlating the electrical conductivity with a chemistry map of the KRS sample or the source formation to interpret effects of mineralogy and maturity.

An embodiment is a method of evaluating KRS, including preparing a KRS sample, selecting one or more regions of interest of the KRS sample, and measuring topography, electrical conductivity, and a mechanical property of the KRS sample at the one or more regions of interest via scanning electron microscopy (for example, AFM). The preparing of the KRS sample may include forming the KRS sample and polishing a surface of the KRS sample, and where polishing includes mechanically polishing the surface or ion milling the surface, or both, to a specified surface roughness of less than 15 micrometers. The selecting of the one or more regions of interest may include selecting a region of interest of the KRS sample via imaging or spectroscopy, or both. The imaging may be the scanning electron microscopy or optical microscopy.

The measuring of electrical conductivity may include mapping the electrical conductivity at microscale or nanoscale, or both, and where the scanning electron microscopy is scanning probe microscopy. The measuring of the electrical conductivity may involve mapping the electrical conductivity to relate the electrical conductivity and the mechanical property to rock structure of the KRS sample. The measuring of electrical conductivity may involve measuring the electrical conductivity via AFM in a first operating mode of an AFM microscope instrument, and measuring the mechanical property (for example, elastic modulus) via AFM in a second operating mode of the AFM microscope instrument. Further, the method may include correlating the electrical conductivity with the mechanical property. The method may include correlating the electrical conductivity with the mechanical property at same locations in the KRS sample, where the electrical conductivity and the mechanical property are measured at the same locations. Moreover, the method may include measuring porosity of the KRS sample at the one or more regions of interest via the scanning electron microscopy. Thus, the correlating may include matching the electrical conductivity and porosity with the mechanical property at specific locations in the one or more regions of interest on the KRS sample at microscale or smaller, and where the microscale or smaller is less than one millimeter. In addition, the method may include capturing, via the spectroscopy, chemical information of the KRS sample at spatial resolution of less than 1 mm. The method may include identifying, via spectroscopy, chemical components of the KRS sample, where the chemical components include organic components and inorganic components. The spectroscopy can include EDS, AFM-IR, micro-FTIR, or fluorescence spectroscopy, or any combinations thereof. The method may include imaging the KRS sample, where identifying chemical components includes identifying the chemical components of the KRS sample spatially via the spectroscopy and the imaging. The imaging (for example, AFM topography) may be performed contemporaneous with measuring the electrical conductivity or with measuring the mechanical property. As indicated, the method may include associating the electrical conductivity with the chemical components spatially. For example, the method may include correlating the electrical conductivity with a chemistry map of the KRS sample to interpret effects of mineralogy and maturity, where the chemistry map is determined by at least spectroscopy such as EDS, AFM-IR, micro-FTIR, or fluorescence spectroscopy.

The method may include linking the electrical conductivity and the chemical components to mineralogy, lithology, thermal maturity, and domain orientation of bulk KRS, where the bulk KRS is bulk KRS of the KRS sample or bulk KRS of a source rock formation from which the KRS sample was collected. The method may include upscaling the electrical conductivity as measured to field data of a KRS source formation from which the KRS sample was collected. The method may include linking the electrical conductivity (nanoscale electrical-conductivity measurements) to resistivity logs of a KRS source formation. The method may include performing pyrolysis (for example, Rock-Eval® pyrolysis) on material of the KRS sample or on material from which the KRS sample was prepared, and interpreting thermal maturity of the KRS sample correlative with results of the pyrolysis.

Another embodiment is a method of evaluating KRS including identifying, via spectroscopy, chemical components of a KRS sample. In one implementation, the spectroscopy is EDS. The method may include preparing the KRS sample from a sample of a KRS geological formation, where preparing includes polishing the KRS sample. The method includes measuring, via AFM, electrical conductivity of the KRS sample and a mechanical property of the KRS sample. The measuring of the electrical conductivity includes mapping the electrical conductivity at microscale or smaller. The method includes correlating spatially the electrical conductivity, the mechanical property, and the chemical components at microscale or smaller. The method may include evaluating a KRS source formation based at least in part on the correlating, where the chemical components include minerals and organic components. Furthermore, the method may include correlating the electrical conductivity to resistivity logs of a KRS source formation. The method may include linking of the electrical conductivity of the chemical components with at least one of mineralogy, lithology, thermal maturity, or domain orientation of bulk KRS. The method may include upscaling the electrical conductivity as measured and the mechanical property as measured to field data of a KRS geological formation from which the KRS sample was obtained.

Yet another embodiment is a system to evaluate KRS, including a sample preparation system to polish a surface of a KRS sample. The sample preparation system may include a mechanical polisher or an argon ion mill, or both, to polish the KRS sample. The system includes a spectrometer to identify chemical components of the KRS sample. The spectrometer may be an EDS instrument, AFM-IR instrument, a micro-FTIR instrument, or a fluorescence spectroscopy instrument. The system includes an AFM instrument to measure electrical conductivity of the KRS sample and a mechanical property of the KRS sample, and to map the electrical conductivity at microscale or smaller. The system includes a computing system to correlate spatially the electrical conductivity, the mechanical property, and the chemical components at microscale or smaller. The computing system may upscale the electrical conductivity as measured and the mechanical property as measured to field data of a KRS source formation from which the KRS sample was collected. The computing system may link the electrical conductivity, the mechanical property, and the chemical components as spatially correlated to mineralogy, lithology, thermal maturity, and domain orientation of bulk KRS, and where the bulk KRS is bulk KRS of the KRS sample or bulk KRS of a source formation from which the KRS sample was collected.

A number of implementations have been described. Nevertheless, it will be understood that various modifications may be made without departing from the spirit and scope of the disclosure.

What is claimed is:

1. A method of evaluating kerogen-rich shale (KRS), comprising:
preparing a KRS sample;
selecting one or more regions of interest of the KRS sample;

measuring topography, electrical conductivity, and a mechanical property of the KRS sample at the one or more regions of interest via scanning probe microscopy.

2. The method of claim 1, wherein measuring electrical conductivity comprises mapping the electrical conductivity at microscale or nanoscale, or both.

3. The method of claim 1, wherein selecting the one or more regions of interest comprises selecting a region of interest of the KRS sample via imaging or spectroscopy, or both.

4. The method of claim 3, wherein the imaging comprises scanning electron microscopy or optical microscopy.

5. The method of claim 3, comprising capturing, via the spectroscopy, chemical information of the KRS sample at spatial resolution of less than 1 millimeter (mm).

6. The method of claim 1, comprising measuring porosity of the KRS sample at the one or more regions of interest via the scanning electron microscopy.

7. The method of claim 1, comprising correlating the electrical conductivity with the mechanical property.

8. The method of claim 7, wherein correlating comprises matching the electrical conductivity with the mechanical property at specific locations in the one or more regions of interest on the KRS sample at microscale or smaller, and wherein the microscale or smaller is less than one millimeter.

9. The method of claim 1, comprising correlating the electrical conductivity with a chemistry map of the KRS sample to interpret effects of mineralogy and maturity, wherein the chemistry map is determined by at least spectroscopy.

10. The method of claim 9, wherein the spectroscopy comprises energy dispersive X-ray spectroscopy (EDS).

11. The method of claim 9, wherein the spectroscopy comprises at least one of atomic force microscopy (AFM)-infrared red spectroscopy (AFM-IR), micro-Fourier-transform infrared spectroscopy (micro-FTIR), or fluorescence spectroscopy.

12. The method of claim 1, comprising correlating the electrical conductivity with the mechanical property at same locations in the KRS sample, wherein measuring comprises measuring the electrical conductivity and the mechanical property at the same locations.

13. The method of claim 1, wherein the scanning probe microscopy comprises atomic force microscopy (AFM).

14. The method of claim 13, wherein measuring electrical conductivity comprises measuring the electrical conductivity via the AFM in a first operating mode of an AFM microscope instrument, wherein measuring the mechanical property comprises measuring the mechanical property via the AFM in a second operating mode of the AFM microscope instrument, and wherein the mechanical property comprises elastic modulus.

15. The method of claim 1, comprising identifying, via spectroscopy, chemical components of the KRS sample, wherein the chemical components comprise organic components and inorganic components.

16. The method of claim 15, comprising associating the electrical conductivity with the chemical components spatially.

17. The method of claim 15, wherein the spectroscopy comprises EDS, AFM-IR, micro-FTIR, or fluorescence spectroscopy, or any combinations thereof.

18. The method of claim 15, comprising imaging the KRS sample, wherein identifying comprises identifying chemical components of the KRS sample spatially via the spectroscopy and the imaging.

19. The method of claim 18, wherein the imaging is performed contemporaneous with measuring the electrical conductivity or with measuring the mechanical property.

20. The method of claim 18, wherein the imaging comprises AFM topography.

21. The method of claim 15, comprising:
performing pyrolysis on material of the KRS sample or on material from which the KRS sample was prepared; and
interpreting thermal maturity of the KRS sample correlative with results of the pyrolysis.

22. The method of claim 21, wherein the pyrolysis comprises Rock-Eval® pyrolysis.

23. The method of claim 15, comprising linking the electrical conductivity and the chemical components to mineralogy, lithology, thermal maturity, and domain orientation of bulk KRS, wherein the bulk KRS comprises bulk KRS of the KRS sample or bulk KRS of a source rock formation from which the KRS sample was collected.

24. The method of claim 1, wherein preparing the KRS sample comprises forming the KRS sample and polishing a surface of the KRS sample, and wherein polishing comprises mechanically polishing the surface or ion milling the surface, or both, to a specified surface roughness of less than 15 micrometers.

25. The method of claim 1, comprising upscaling the electrical conductivity as measured to field data of a KRS source formation from which the KRS sample was collected, and wherein measuring the electrical conductivity comprises mapping the electrical conductivity to relate the electrical conductivity and the mechanical property to rock structure of the KRS sample.

26. The method of claim 1, comprising linking the electrical conductivity comprising nanoscale electrical-conductivity measurements to resistivity logs of a KRS source formation.

27. A method of evaluating kerogen-rich shale (KRS), comprising:
identifying, via spectroscopy, chemical components of a KRS sample;
measuring, via atomic force microscopy (AFM), electrical conductivity of the KRS sample and a mechanical property of the KRS sample, wherein measuring electrical conductivity comprises mapping the electrical conductivity at microscale or smaller; and
correlating spatially the electrical conductivity, the mechanical property, and the chemical components at microscale or smaller.

28. The method of claim 27, wherein the spectroscopy comprises energy dispersive X-ray spectroscopy (EDS).

29. The method of claim 27, comprising evaluating a KRS source formation based at least in part on the correlating, wherein the chemical components comprise minerals and organic components.

30. The method of claim 27, comprising correlating the electrical conductivity to resistivity logs of a KRS source formation.

31. The method of claim 27, comprising linking the electrical conductivity of the chemical components with at least one of mineralogy, lithology, thermal maturity, or domain orientation of bulk KRS.

32. The method of claim 27, comprising upscaling the electrical conductivity as measured and the mechanical property as measured to field data of a KRS geological formation from which the KRS sample was obtained.

33. The method of claim 27, comprising preparing the KRS sample from a sample of a KRS geological formation, wherein preparing comprises polishing the KRS sample.

34. A system to evaluate kerogen-rich shale (KRS), comprising:
   a sample preparation system to polish a surface of a KRS sample;
   a spectrometer to identify chemical components of the KRS sample;
   an atomic force microscopy (AFM) instrument to measure electrical conductivity of the KRS sample and a mechanical property of the KRS sample, and to map the electrical conductivity at microscale or smaller; and
   a computing system to correlate spatially the electrical conductivity, the mechanical property, and the chemical components at microscale or smaller.

35. The system of claim 34, wherein the sample preparation system comprises a mechanical polisher or an argon ion mill, or both, to polish the KRS sample, and wherein the spectrometer comprises an energy dispersive X-ray spectroscopy (EDS) instrument.

36. The system of claim 34, wherein the spectrometer comprises at least one of an AFM-infrared red spectroscopy (AFM-IR) instrument, a micro-Fourier-transform infrared spectroscopy (micro-FTIR) instrument, or a fluorescence spectroscopy instrument.

37. The system of claim 34, wherein the computing system to link the electrical conductivity, the mechanical property, and the chemical components as spatially correlated to mineralogy, lithology, thermal maturity, and domain orientation of bulk KRS, and wherein the bulk KRS comprises bulk KRS of the KRS sample or bulk KRS of a source formation from which the KRS sample was collected.

38. The system of claim 34, wherein the computing system to upscale the electrical conductivity as measured and the mechanical property as measured to field data of a KRS source formation from which the KRS sample was collected.

* * * * *